US011231120B2

(12) United States Patent
Gagne et al.

(10) Patent No.: US 11,231,120 B2
(45) Date of Patent: *Jan. 25, 2022

(54) FLEXIBLE TUBING MANAGEMENT SYSTEM FOR PHARMACEUTICAL, BIOPROCESS APPLICATIONS, AND FOOD/DAIRY APPLICATIONS

(71) Applicant: Repligen Corporation, Waltham, MA (US)

(72) Inventors: Michael C. Gagne, Carson City, NV (US); Dean C. Richards, Simi Valley, CA (US); Steven V. Cates, Lakewood, CA (US); Scott Bendon, Wales (GB)

(73) Assignee: Repligen Corporation, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/794,160

(22) Filed: Feb. 18, 2020

(65) Prior Publication Data

US 2020/0326004 A1 Oct. 15, 2020

Related U.S. Application Data

(63) Continuation of application No. 15/759,794, filed as application No. PCT/US2016/051714 on Sep. 14, 2016, now Pat. No. 10,612,681.

(Continued)

(51) Int. Cl.
*F16L 3/26* (2006.01)
*F16K 27/00* (2006.01)
(Continued)

(52) U.S. Cl.
CPC ............... *F16K 27/00* (2013.01); *A23C 7/00* (2013.01); *A61J 3/00* (2013.01); *A61M 5/1418* (2013.01);
(Continued)

(58) Field of Classification Search
CPC ...... F16L 3/13; F16L 3/24; F16L 3/26; A61M 5/1413; A61M 5/1418; A61J 3/00
See application file for complete search history.

(56) References Cited

U.S. PATENT DOCUMENTS 2,825,524 A ‡ 3/1958 Fox .................... F16K 7/061
251/8
2,931,387 A ‡ 4/1960 Fleming ............ F16K 11/22
137/88

(Continued)

FOREIGN PATENT DOCUMENTS

DE 42 24 167 1/1994
DE 42 24 167 A1 ‡ 1/1994 .......... A61M 5/1418
(Continued)

OTHER PUBLICATIONS

PCT Written Opinion of the International Search Authority for PCT/US10/34371, Applicant: AlphaBio, Inc., Form PCT/ISA/237, dated Jul. 1, 2010 (7 pages).‡

(Continued)

*Primary Examiner* — Kevin F Murphy
(74) *Attorney, Agent, or Firm* — Kacvinsky Daisak Bluni PLLC

(57) ABSTRACT

A system for managing flexible conduit or tubing used in pharmaceutical, bioprocess, or food/dairy applications includes a segment of flexible conduit or tubing and a plurality of conduit tracks, each conduit track including a conduit channel disposed on a first side thereof and extending along the length of each respective conduit track and dimensioned to receive the segment of flexible conduit or tubing therein, each conduit track further including a connector channel disposed on a second, opposing side and extending along the length of each respective conduit track and containing the one or more connectors that connect (Continued)

adjacent conduit tracks. The conduit tracks can be connected to each other or other process components.

18 Claims, 10 Drawing Sheets

Related U.S. Application Data

(60) Provisional application No. 62/218,974, filed on Sep. 15, 2015.

(51) Int. Cl.
| | | |
|---|---|---|
| *F16K 7/07* | (2006.01) | |
| *F16L 3/24* | (2006.01) | |
| *A61M 5/14* | (2006.01) | |
| *F16L 3/13* | (2006.01) | |
| *A23C 7/00* | (2006.01) | |
| *A61J 3/00* | (2006.01) | |
| *A61M 39/28* | (2006.01) | |

(52) U.S. Cl.
CPC ............... *F16K 7/07* (2013.01); *F16L 3/13* (2013.01); *F16L 3/24* (2013.01); *F16L 3/245* (2019.08); *A61M 5/1413* (2013.01); *A61M 39/28* (2013.01); *F16L 3/26* (2013.01)

(56) References Cited

U.S. PATENT DOCUMENTS

| | | | | |
|---|---|---|---|---|
| 4,254,797 | A ‡ | 3/1981 | Mayeaux | G01N 33/0006 137/55 |
| 4,618,114 | A ‡ | 10/1986 | McFarland | F16L 3/13 248/22 |
| 4,895,341 | A ‡ | 1/1990 | Brown | F16K 7/061 251/63 |
| 4,993,456 | A ‡ | 2/1991 | Sule | F16K 7/045 137/55 |
| 5,078,683 | A ‡ | 1/1992 | Sancoff | A61M 5/14228 604/67 |
| 5,165,874 | A * | 11/1992 | Sancoff | A61M 5/14228 128/DIG. 12 |
| 5,197,708 | A ‡ | 3/1993 | Campau | F16K 7/061 251/8 |
| 5,350,290 | A ‡ | 9/1994 | Honings | A21C 5/00 425/31 |
| 5,402,823 | A ‡ | 4/1995 | Cole | F16K 7/063 137/59 |
| 5,529,088 | A * | 6/1996 | Asou | F15B 13/0825 137/343 |
| 5,549,134 | A ‡ | 8/1996 | Browne | F16K 7/16 137/24 |
| 5,901,745 | A ‡ | 5/1999 | Buchtel | F16K 7/06 137/59 |
| 6,036,166 | A ‡ | 3/2000 | Olson | F16K 7/06 222/20 |
| 6,068,751 | A ‡ | 5/2000 | Neukermans | B01L 3/502715 137/60 |
| 6,502,601 | B2 ‡ | 1/2003 | Eidsmore | F15B 13/0814 137/884 |
| 6,543,483 | B2 ‡ | 4/2003 | Johnson | F16K 27/003 137/88 |
| 6,554,589 | B2 ‡ | 4/2003 | Grapes | F04B 43/08 251/7 |
| 6,631,736 | B2 ‡ | 10/2003 | Seitz | F15B 13/0814 137/88 |
| 6,644,353 | B1 ‡ | 11/2003 | Eidsmore | F15B 13/0807 137/88 |
| 6,976,664 | B2 ‡ | 12/2005 | Welch | F16K 7/04 251/4 |
| 7,104,275 | B2 ‡ | 9/2006 | Dille | F16K 7/045 137/48 |
| 7,213,618 | B2 ‡ | 5/2007 | Milburn | F16K 27/003 137/884 |
| 7,367,363 | B2 ‡ | 5/2008 | Friedline | F16L 3/085 138/10 |
| 7,383,853 | B2 ‡ | 6/2008 | Welch | F16L 55/10 137/31 |
| 7,500,949 | B2 * | 3/2009 | Gottlieb | A61B 5/14532 600/300 |
| 7,533,853 | B2 ‡ | 5/2009 | Ogawa | B60R 16/0215 248/73 |
| 8,235,067 | B2 ‡ | 8/2012 | Gagne | F16K 11/027 137/60 |
| 8,282,046 | B2 * | 10/2012 | Harding | A61J 1/00 248/49 |
| 8,656,951 | B2 ‡ | 2/2014 | Gagne | F16K 27/003 137/60 |
| 8,979,070 | B2 ‡ | 3/2015 | Keizer | F16K 7/04 248/221.11 |
| 9,091,380 | B2 ‡ | 7/2015 | Hayashi | F16L 23/10 |
| 9,447,888 | B2 ‡ | 9/2016 | Gagne | F16K 3/30 |
| 10,612,681 | B2 * | 4/2020 | Gagne | F16L 3/24 |
| 2004/0163711 | A1 ‡ | 8/2004 | Varone | F16K 7/065 137/48 |
| 2007/0278155 | A1 ‡ | 12/2007 | Lo | A61M 1/166 210/64 |
| 2007/0295867 | A1 ‡ | 12/2007 | Hennon | F16L 3/1075 248/74 |
| 2008/0035227 | A1 ‡ | 2/2008 | Woods | G01F 1/58 138/10 |
| 2008/0237509 | A1 ‡ | 10/2008 | Yamamoto | F16K 31/122 251/7 |
| 2009/0120503 | A1 ‡ | 5/2009 | Donahue | F16K 17/14 137/1 |
| 2009/0188113 | A1 ‡ | 7/2009 | McKeeth | B23D 21/003 30/106 |
| 2012/0017733 | A1 ‡ | 1/2012 | Gay | A61M 39/284 83/19 |
| 2012/0286110 | A1 ‡ | 11/2012 | Hill | F16L 3/13 248/74.2 |

FOREIGN PATENT DOCUMENTS

| | | | | |
|---|---|---|---|---|
| FR | 2 576 386 | | 7/1986 | |
| FR | 2 576 386 A1 | ‡ | 7/1986 | ............ F16K 11/027 |
| FR | 2 970 315 | | 7/2012 | |
| FR | 2 970 315 A1 | ‡ | 7/2012 | ............... F16L 3/26 |
| GB | 1055426 | ‡ | 1/1967 | |
| JP | 11-82867 | | 3/1999 | |
| JP | 2003-526759 | | 9/2003 | |
| JP | 2004293769 A | ‡ | 10/2004 | |
| JP | 2004293769 A | | 10/2004 | |
| JP | 2013-534822 | | 9/2013 | |
| WO | 97/11296 | | 3/1997 | |
| WO | WO-97/11296 A | ‡ | 3/1997 | |

OTHER PUBLICATIONS

Parker Mitos Product Brochure, Mitos Free Flow Valve, Apr. 29, 2009, http://www.mitostech.com/freelow.html (2 pages).‡
BioWorks LLC Catalog, Model: BSV-H250-Bo, www.BioWorksLLC.com, cited in U.S. Appl. No. 14/165,206 dated Aug. 25, 2014 (6pages).‡
PCT International Search Report for PCT/US10/34371, Applicant: AlphaBio, Inc., Form PCT/ISA/210 and 220, dated Jul. 1, 2010 (4 pages).‡
PCT International Preliminary Report on Patentability (Chapter I of the Patent Cooperation Treaty) for PCT/US2010/034371, Applicant: AlphaBio, Inc., Form PCT/IB/326 and 373, dated Nov. 15, 2011 (9 pages).‡
BioWorks LLC Product Brochure (date: unknown), BSC: Bio Sample Cup, Safe, Sanitary Material Storage, Easton, PA 18042, www.BioWorksLLC.com (6 pages).‡
Notice of Preliminary Rejection dated Dec. 14, 2016 in Korean Patent Application No. 10-2011-7027072, (11pages).‡
Communication from European Patent Office dated Nov. 6, 2017 in European Patent Application No. 10775392.3-1751, (7pages).‡

(56) References Cited

OTHER PUBLICATIONS

The extended European search report dated Nov. 29, 2016 in European Application No. 10775392.3-1751, Applicant: Alphinity, LLC, (10pages).‡
PCT Written Opinion of the International Search Authority for PCT/US2016/051714, Applicant: Alphinity LLC, Form PCT/ISA/237, dated Dec. 7, 2016 (9pages).‡
PCT International Search Report for PCT/US2016/051714, Applicant: Alphinity, LLC, Form PCT/ISA/210 and 220, dated Dec. 7, 2016 (4pages).‡
Response to extended European Search Report dated Nov. 11, 2019 in European Patent Application No. 16847224.9, (36 pages).‡
PCT International Preliminary Report on Patentability (Chapter I of the Patent Cooperation Treaty) for PCT/US2016/051714, Applicant: Alphinity, LLC, Form PCT/IB/326 and 373, dated Mar. 29, 2018 (11pages).‡
Response to Written Opinion dated Oct. 8, 2019 in Singapore Patent Application No. 11201801785W, (2pages).‡
Communication pursuant to Rules 70(2) and 70a(2) EPC dated Apr. 30, 2019 for European Patent Application No. 16847224, (1page).‡
Invitation to Respond to Written Opinion dated May 24, 2019 for Singapore Patent Application No. 11201801785W, (7pages).‡
Supplementary European Search Report dated Apr. 4, 2019 for European Patent Application No. 16847224, (8pages).‡

\* cited by examiner
‡ imported from a related application

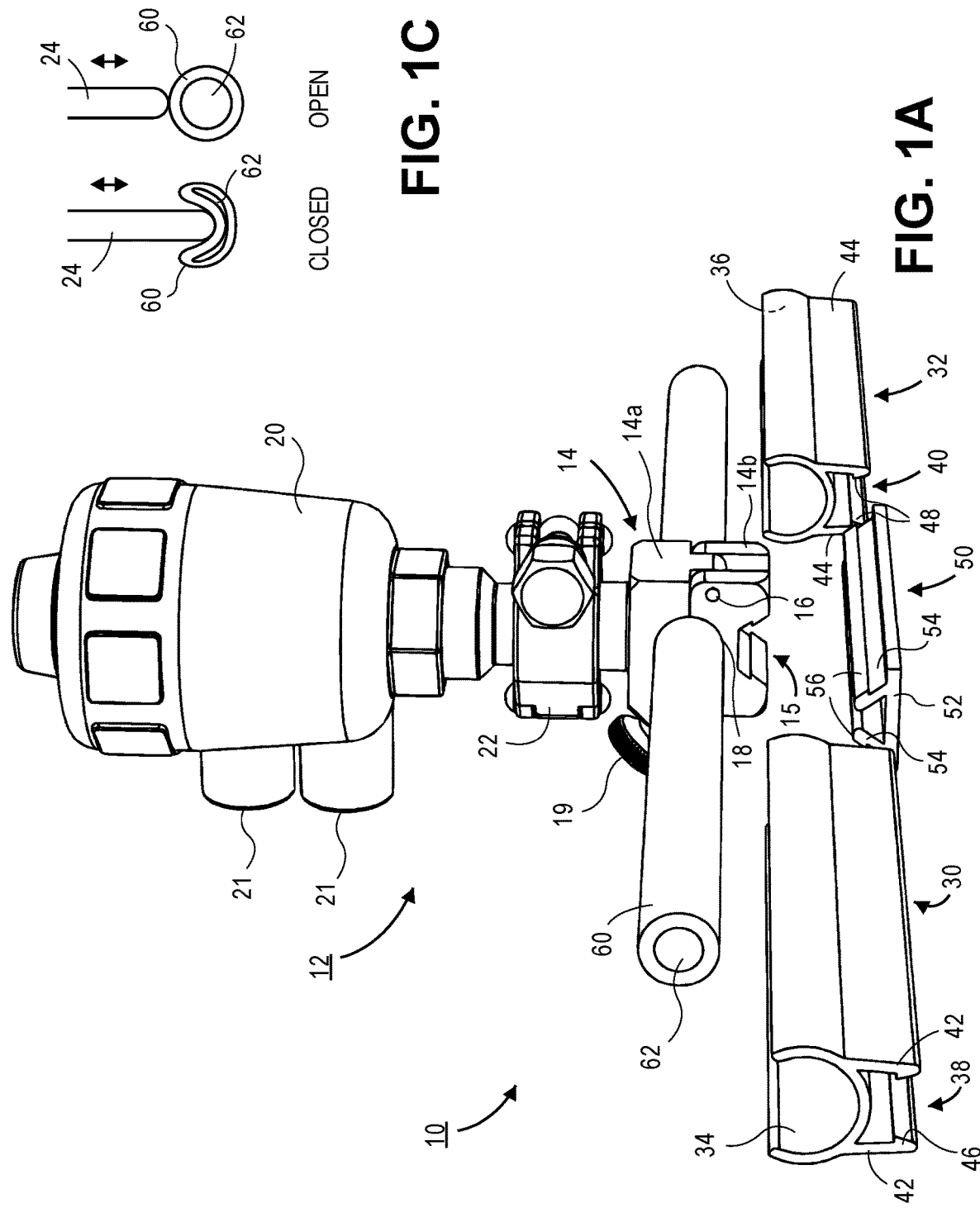

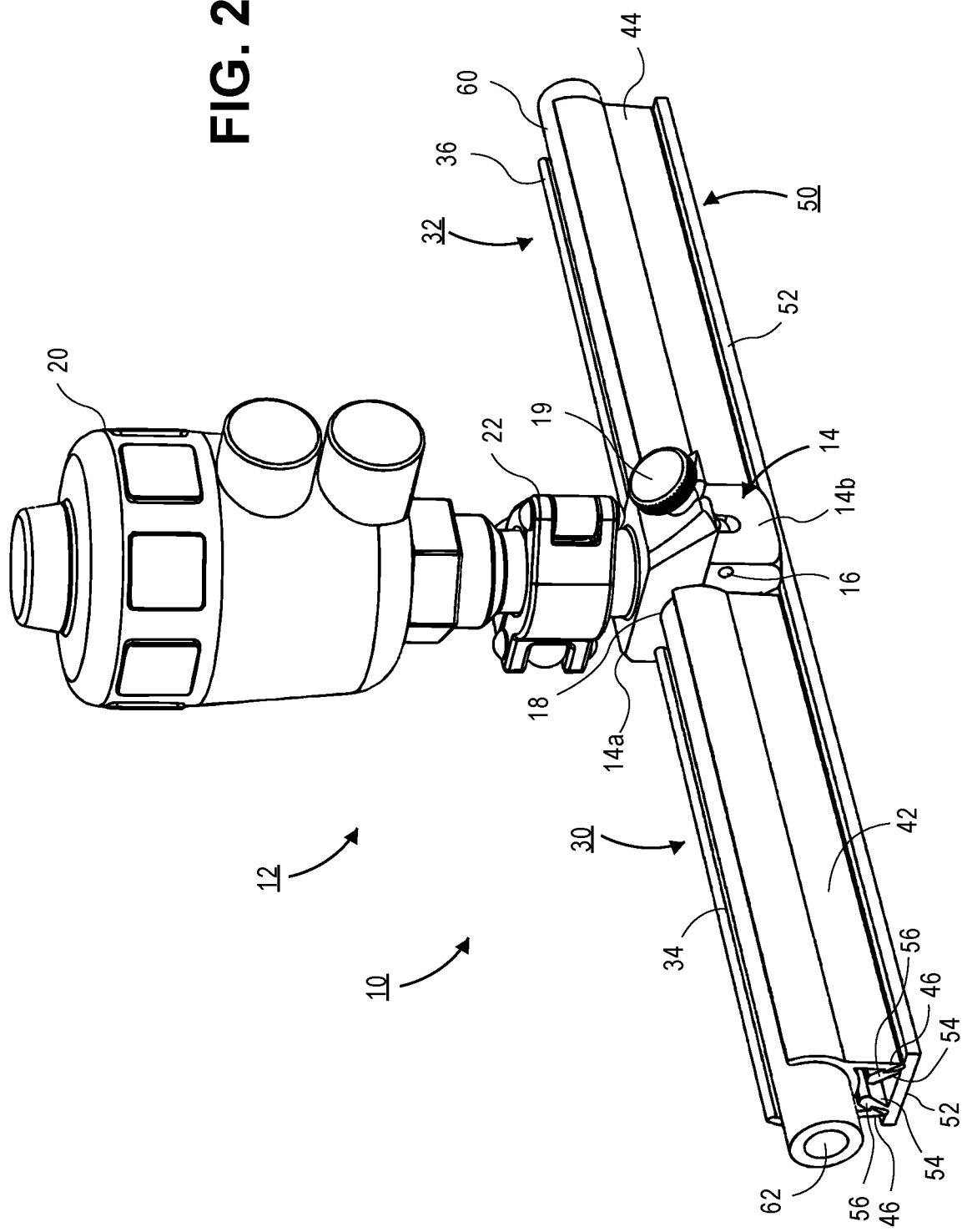

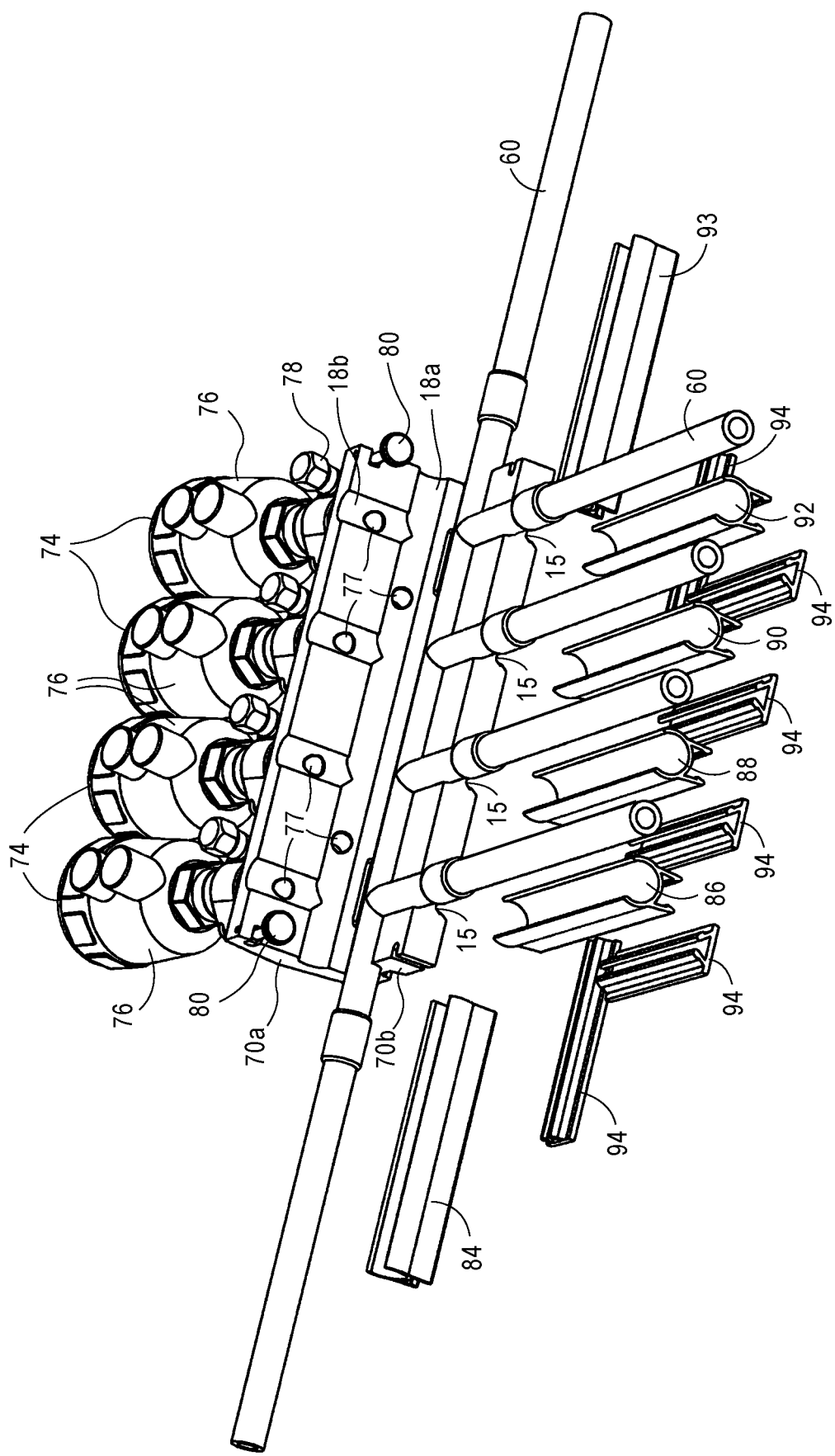

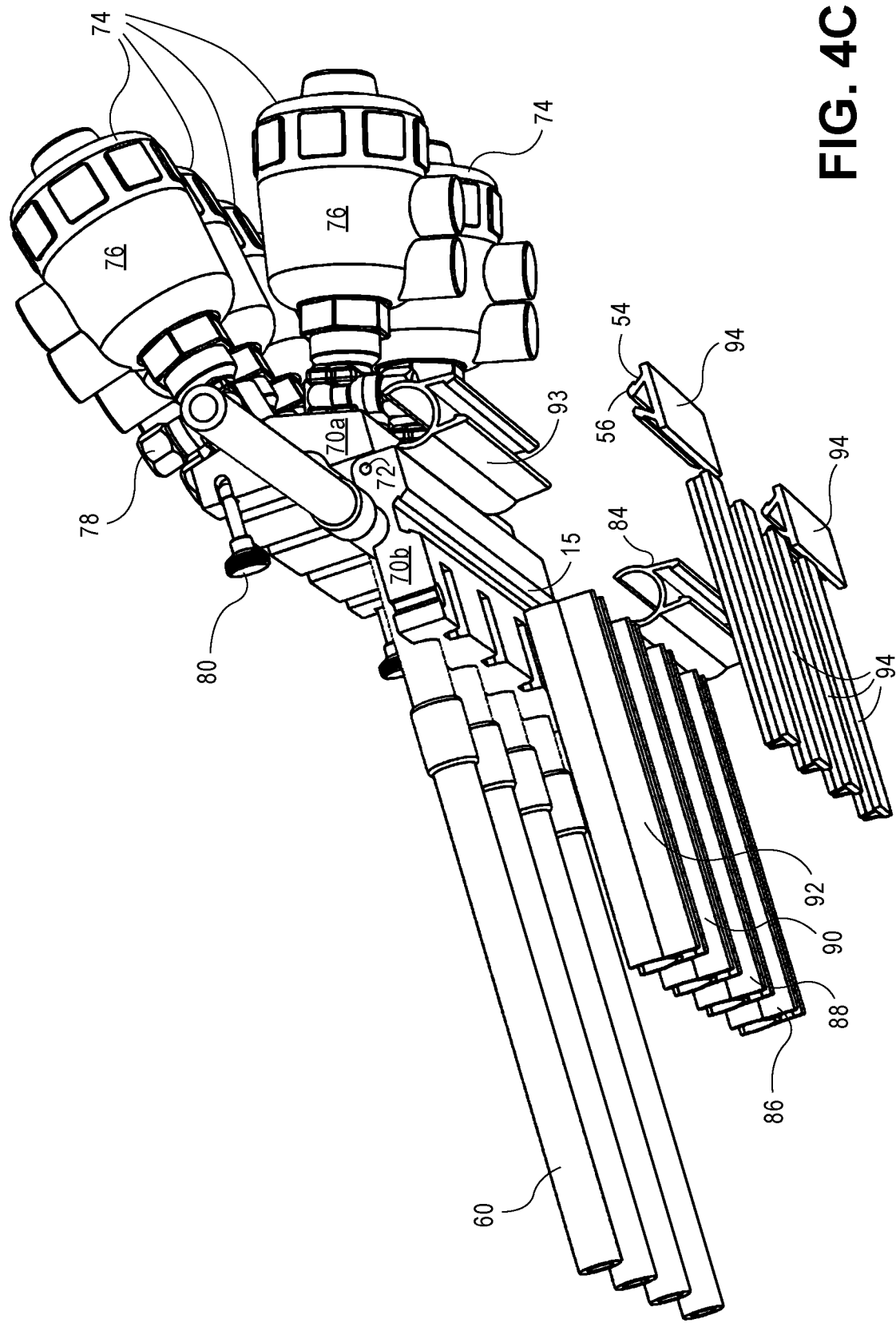

FLEXIBLE TUBING MANAGEMENT SYSTEM FOR PHARMACEUTICAL, BIOPROCESS APPLICATIONS, AND FOOD/DAIRY APPLICATIONS

RELATED APPLICATION

This Application is a continuation of U.S. application Ser. No. 15/759,794 filed on Mar. 13, 2018, now allowed, which is U.S. National Stage filing under 35 U.S.C. § 371 of International Application No. PCT/US2016/051714, filed Sep. 14, 2016, which claims priority to U.S. Provisional Patent Application No. 62/218,974 filed on Sep. 15, 2015, which are hereby incorporated by reference. Priority is claimed pursuant to 35 U.S.C. §§ 119, 120, 371 and any other applicable statute.

FIELD OF THE INVENTION

The field of the invention generally relates to conduit or tubing management systems used in connection with pharmaceutical, bioprocess, or food/dairy applications.

BACKGROUND

Many commercial products are produced using chemical as well as biological processes. Pharmaceuticals, for example, are produced in commercial quantities using scaled-up reactors and other equipment. So-called biologics are drugs or other compounds that are produced or isolated from living entities such as cells or tissue. Biologics can be composed of proteins, nucleic acids, or complex combinations of these substances. They may even include living entities such as cells. In order to produce biologics on a commercial scale, sophisticated and expensive equipment is needed. In both pharmaceutical and biologics, for example, various processes need to occur before the final product is obtained. For example, in the case of biologics, cells may be grown in a growth chamber or the like and nutrients may need to be carefully modulated into the growth chamber. Waste products produced by cells may also have to be removed on a controlled basis from the fermentation chamber. As another example, biologic products produced by living cells or other organisms may need to be extracted and concentrated. This process may involve a variety of filtration and separation techniques.

Because there are a number of individual processes required to be produce the final product, various reactants, solutions, and washes are often pumped or otherwise transported to various subsystems using conduits and associated valves. This same organizational complexity may also be found in some commercial food and dairy applications. These systems may be quite cumbersome and organizationally complex due to the large numbers of conduits, valves, sensors, and the like that may be needed in such systems. Not only are these systems visually complex (e.g., resembling spaghetti) they also include many components that are required to be sterilized between uses to avoid cross-contamination issues. Indeed, the case of drug and biologic preparation, the Federal Food and Drug Administration (FDA) is becoming increasingly strict on cleaning, sterilization or bio-burden reduction procedures that are required for drug and pharmaceutical preparations. This is particularly of a concern because many of these products are often produced in batches which would require repeated cleaning, sterilization or bio-burden reduction activities on a variety of components.

More recently, disposable solutions have been proposed that utilize flexible (e.g., silicone) tubing during the manufacturing process. The flexible tubing may be discarded after use and replaced with new tubing, thereby avoiding the need to sterilize some or all of the equipment. While the use of flexible, disposable tubing provides advantages there is still the problem of managing the tubing and connected components within the overall system. As noted above, the process operations involved in pharmaceutical manufacturing and other bioprocess operations and the like are organizationally complex which require a number of different conduit segment lengths or runs that go between various components such as valves, sensors, filters, pumps, chromatography columns, elution columns, reactors, and the like. Without proper management (or even with organization) of the various tubing segments and associated process components, the system may still resemble spaghetti. Not only is this visually complex, there often are components within the system that may need to be to be adjusted, inspected, or changed-out. If there is poor organization of the system, this may interfere with the ability to properly and efficiently operate and maintain the manufacturing system. There thus is a need for a solution to better organize and manage tubing and process operations that are used in connection with pharmaceutical, bioprocess, and food/dairy manufacturing systems.

SUMMARY

In one embodiment of the invention, a system for managing flexible conduit (e.g., tubing) used in pharmaceutical, bioprocess, or food/dairy applications includes a plurality of conduit tracks which are connected either end-to-end to each other or to other process components using connectors to spatially manage and organize process components. Organizational complexity is reduced by using the conduit tracks to spatially position the flexible tubing and other components. The system is modular and can be connected in any number of desired configurations. The flexible tubing can be easily inserted into or removed from the conduit tracks which contain open channels that receive the flexible tubing. Process components such as valves, sensors, filters, elution columns, pumps, reservoirs, and the like can be integrated at appropriate points within the fluid pathway using a common mounting scheme that interfaces with the conduit tracks. The conduit tracks (and other components) can be mounted to a scaffold or support. The scaffold or support may be stationary or it may be mobile (e.g., a cart). The conduit tracks may have a number of shapes and lengths so that the fluid flow paths can be created and established in an organized and clean fashion that aids in the setup, operation, and maintenance of the system. For example, the flexible conduit or tubing that is used may be disposable and quickly swapped out and replaced with another flexible conduit or tubing. Downtime before setup and between runs is thus minimized.

In one embodiment of the invention, a system for managing flexible conduit or tubing used in pharmaceutical, bioprocess, or food/dairy applications includes a segment of flexible conduit or tubing and a plurality of conduit tracks. Each conduit track includes a conduit channel disposed on a first side thereof and extending along the length of each respective conduit track and dimensioned to receive the segment of flexible conduit or tubing therein, each conduit track further including a connector channel disposed on a second, opposing side and extending along the length of each respective conduit track and containing the one or more connectors that connect adjacent conduit tracks. The conduit tracks may also be connected to other processing components such as a pump, valve, sensor, filter, chromatography column, elution column, reactor, reservoir, and manifold interposed between at least two conduit tracks.

In another embodiment, a system for managing flexible conduit or tubing used in pharmaceutical, bioprocess, or food/dairy applications includes a plurality of conduit tracks configured to connect to one another in an end-to-end fashion with one or more connectors, each conduit track including an conduit channel disposed on a first side thereof and extending along the length of each respective conduit track and dimensioned to receive a flexible conduit or tubing therein, each conduit track further including a connector channel disposed on a second, opposing side and extending along the length of each respective conduit track and containing the one or more connectors. A flexible conduit or tubing is disposed in the conduit channel.

In still another embodiment, a system for managing flexible conduit or tubing used in pharmaceutical, bioprocess, or food/dairy applications includes a valve including a hinged valve body having a first body portion and a second body portion connected to one another at a hinge, the first body portion and the second body portion defining a passageway extending through the valve body when in a closed state, the valve further including an actuator disposed on the valve body and having a pinching element configured to selectively move into and out of the passageway, wherein one of the first body portion and the second body portion includes a mounting channel disposed therein and oriented along the direction of the passageway. A flexible conduit or tubing extends through the passageway of the valve body. The system includes a first conduit track disposed on one side of the valve body, the first conduit track having a conduit channel extending along the length of the first conduit track and dimensioned to receive the flexible conduit or tubing therein, the first conduit track further including a connector channel extending along the length of the first conduit track. A second conduit track is disposed on an opposite side of the valve body, the second conduit track having a conduit channel extending along the length of the second conduit track and dimensioned to receive the flexible conduit or tubing therein, the second conduit track further having a connector channel extending along the length of the second conduit track. The system includes at least one connector disposed in the mounting channel and extends into the connector channel of the first conduit track and the connector channel of the second conduit track, wherein the valve body is secured to the connector.

BRIEF DESCRIPTION OF THE DRAWINGS

FIG. 1A illustrates a system for managing flexible tubing according to one embodiment. An exploded, perspective view of a single valve that is located between two segments of conduit track is illustrated. Also seen is the connector member that connects the two segments of conduit track and the valve.

FIG. 1C illustrates a schematic view of a valve actuator that is used to pinch flexible tubing. The pinching element extends and pinches the flexible tubing and creates a "Closed" state. When the actuator is retracted, the flexible tubing is not pinched and creates an "Open" state.

FIG. 2A illustrates a perspective view of the system for managing flexible tubing according to the embodiment of FIGS. 1A and 1B. The flexible conduit is passing through the passageway of the valve and being positioned within the conduit channel of the two conduit tracks that book-end the valve. A connector extends the length of conduit tracks and valve body.

FIG. 4A illustrates a perspective view of another multi-valve embodiment.

FIG. 4C illustrates yet another perspective view of the multi-valve embodiment of FIG. 4A.

FIG. 5A illustrates the modular components prior to assembly.

DETAILED DESCRIPTION OF THE ILLUSTRATED EMBODIMENTS

Figure 1B:
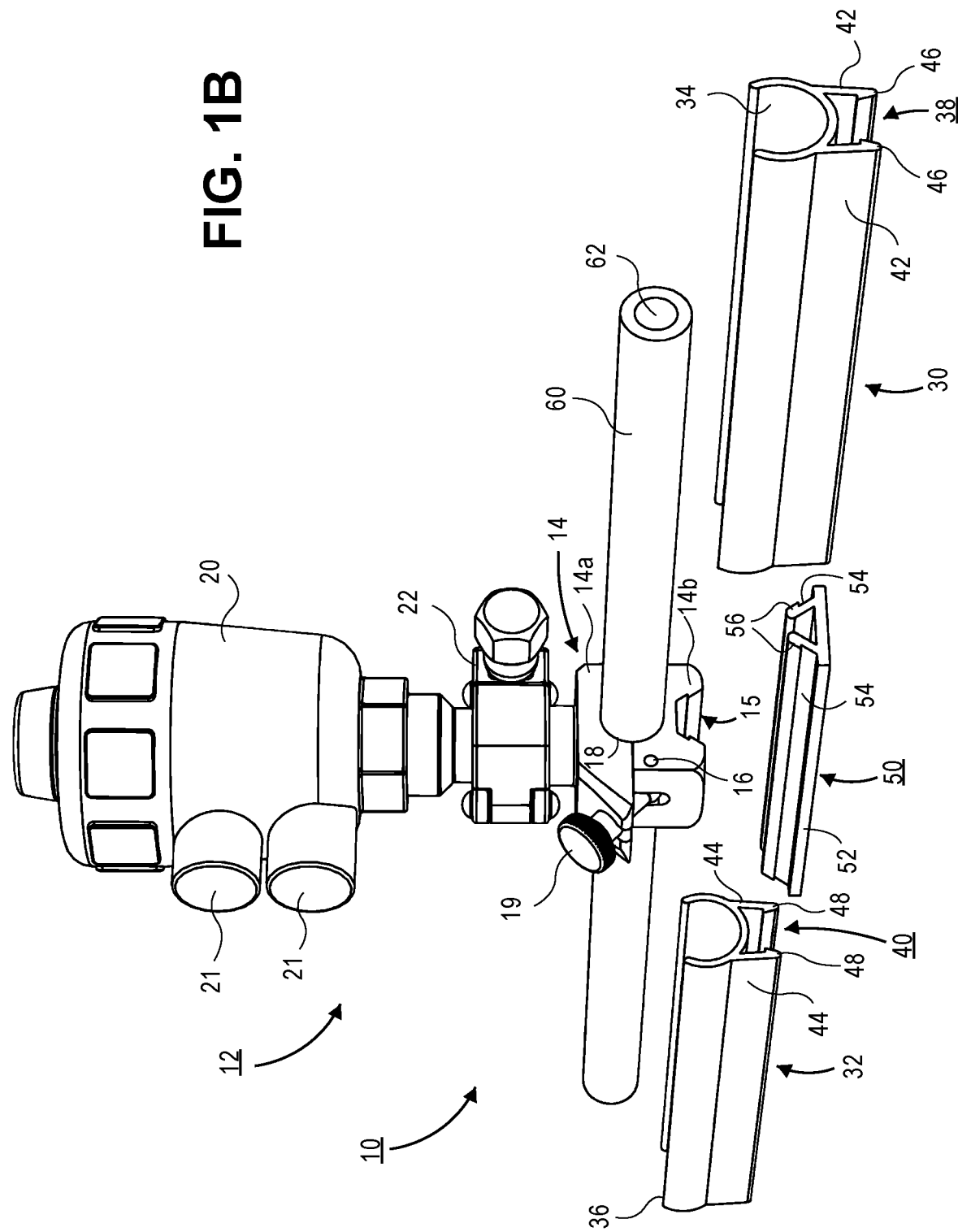
FIG. 1B illustrates another exploded, perspective view of the system for managing flexible tubing illustrated in FIG. 1A.

FIGS. 1A and 1B illustrate a system 10 for managing flexible conduit (e.g., tubing) according to one embodiment. As noted herein, the system 10 has particular applicability for pharmaceutical, chemical, bioprocess, and food/diary manufacturing operations. The system 10 is used, for example, to manage the layout and physical location of various components used in a fluid-based manufacturing process. FIGS. 1A and 1B illustrate a valve 12 being interposed between and connected to two segments of conduit track 30, 32. A flexible conduit 60 is illustrated and passes through the valve 12 and is secured in place to the two segments of conduit track 30, 32 as explained below. The flexible conduit 60 is used to carry a fluid, typically although not exclusively at low pressures. The flexible conduit 60 may include silicone however other materials may be used. These include, for example, a polymer such as thermoplastic elastomers (TPE), thermoplastic rubber (TPR), or the like. The flexible conduit 60 may be unreinforced or reinforced. The flexible conduit 60 includes a central lumen through which fluid passes. The flexible conduit 60 may have a variety of sizes. For example, without limiting the invention, the flexible conduit 60 may have an internal diameter of 0.375 inches and an outer diameter of 0.625 inches. Of course, this is just illustrative and other diameters may also be used. The invention is not limited by the size of the flexible conduit 60 that is used.

Still referring to FIGS. 1A and 1B, a valve 12 is illustrated being secured around the flexible conduit 60. The valve 12 includes a valve body 14 that is hinged via hinge 16 and forms first and second body portions 14a, 14b. The valve body 14 is typically made from a metallic material but it could also be formed from a suitably hard plastic or other polymer material. The first and second body portions 14*a*, 14*b*, when in a closed state (as illustrated in FIGS. 1A and 1B), define a passageway 18 that extends through the valve body 14 that receives the flexible conduit 60. The first and second body portions 14*a*, 14*b* may be secured in the closed state using a fastener 19. The fastener 19 as illustrated in FIGS. 1A and 1B may include a threaded latch and knob that can be tightened or loosened on the threaded latch to selectively close/open the valve body 14. The size and shape of the passageway 18 is such that the flexible conduit 60 fits snuggly therein. For example, the inner diameter of the passageway 18 may closely match the outer diameter of the flexible conduit 60. As seen in FIG. 1A, a valve actuator 20 is disposed on the valve body 14. In this embodiment, a clamp 22 is used to secure the valve actuator 20 to the valve body 14. The use of the clamp 22 is optional, however. In some embodiments, the valve actuator 20 may be directly integrated with the valve body 14. The actuator 20 includes a pinching element 24 as seen in FIG. 1C that moves in the direction of the arrow to selectively close/open the central lumen 62 of the flexible conduit 60. The actuator 20 may be moved using any number approaches. For example, the actuator 20 may be pneumatically actuated valves using air ports 21. The actuator 20 may also be manually advanced/ retracted using a bonnet or the like that is manually rotated. The actuator 20 may also be actuated using a manually-activated toggle-type mechanism that does not require rotation of a bonnet or the like. This enables one to rapidly switch the valve between on/off states.

Still referring to FIGS. 1A and 1B, conduit tracks 30, 32 are illustrated adjacent to the valve 12 with each conduit track 30, 32 being located on opposing sides of the valve 12. The conduit tracks 30, 32 are used to hold the flexible conduit 60 in place in the desired spatial configuration (e.g., length, shape, and the like). The conduit tracks 30, 32 may be made of any material (e.g., polymer or plastic-based) and are typically rigid or semi-rigid. In this example, the conduit tracks 30, 32 are straight segments of track although other shapes may be used (e.g., curves, bends and the like may be integrated into the track). Each conduit track 30, 32 includes a respective conduit channel 34, 36 that extends along the length of each conduit track 30, 32 and is dimensioned to receive the flexible conduit 60. The conduit channels 34, 36 may be continuous (as illustrated) or interrupted along the length. In this embodiment, the conduit channels 34, 36 are C-shaped or semi-annular so that that flexible conduit 60 can be clipped into position. The flexible conduit 60 is pressed into the conduit channels 34, 36 and is retained by the C-shaped structure (some compression of the flexible conduit 60 during insertion and removal may occur). The opening of each conduit channel 34, 36 may be smaller than the outer diameter of the flexible conduit 60 so that the flexible conduit 60 is securely retained therein. Each conduit track 30, 32 includes a respective connector channel 38, 40 as illustrated in FIGS. 1A and 1B. The connector channel 38, 40 is located on an opposing side of the conduit channels 34, 36 in the illustrated embodiment. Each connector channel 38, 40 is formed by a pair of walls 42, 44 that extend from the conduit channels 34, 36 and terminate at respective retaining tabs 46, 48. The retaining tabs 46, 48 are used to retain a connector that is inserted into the connector channels 38, 40 as described below.

As seen in FIGS. 1A and 1B, a connector 50 is used to connect the valve body 14 to the conduit tracks 30, 32. The connector 50 may formed from a rigid piece of material (e.g., polymer, plastic-based, or even metal) that is used to connect the valve 12 to the adjacent conduit tracks 30, 32. As seen in FIGS. 1A and 1B, the connector 50 includes a base 52 with a pair of retaining members 54 that extend along a length of the connector 50. The pair of retaining members 54 may include angled walls or edges as seen in FIG. 1A. The retaining members 54 may be continuous along the length of the connector 50 or they may be interrupted. The retaining members 54 in FIGS. 1A and 1B have a corresponding tab 56 along their length that engages with the corresponding tabs 46, 48 in the connector channels 38, 40. In this regard, the connector 50 is secured securely to the connector channels 38, 40 and the valve body 14. The valve body 14 includes a mounting channel 15 that is located in in the valve body 14 and configured to mate with the retaining members 54 and tab 56 of the connector 50. The mounting channel 15 as illustrated in FIGS. 1A and 1B is a notched channel located in one of the two halves 14*a*, 14*b* of the valve body 14 that has notched surfaces that engage with the retaining members 54 and tab 56. The connector 50 can be inserted laterally into the connector channels 38, 40 and the mounting channel 15. Alternatively, in some embodiments, the connector 50 may be pressed directly into the connector channels 38, 40 and mounting channel 15 whereby the retaining members 54 flex and then lock into place (e.g., the connector 50 snaps into place after being pressed into the mounting channel 15 and connector channels 38, 40).

Figure 2B:
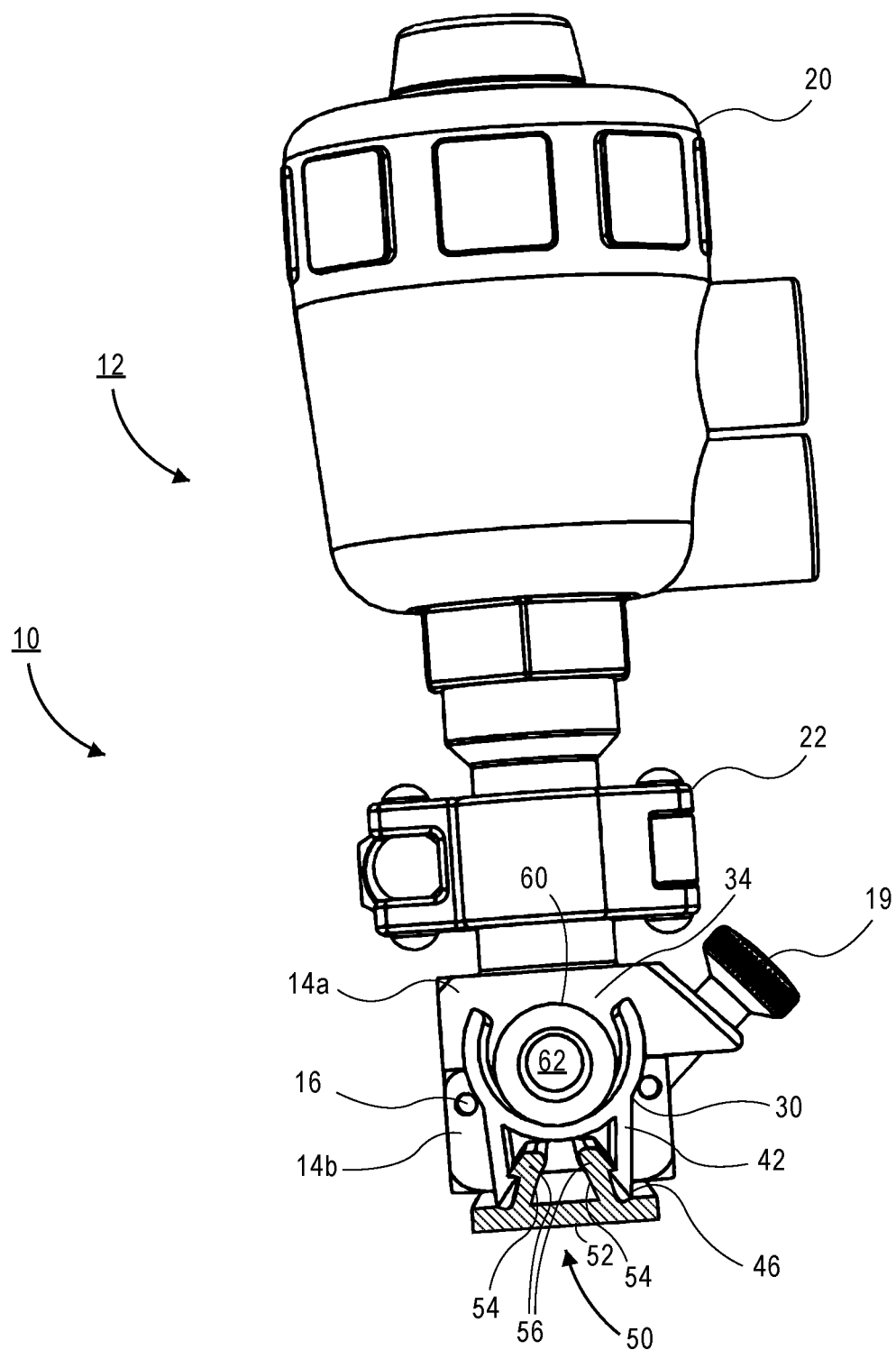
FIG. 2B illustrates an end view of the system of FIG. 2A. The flexible conduit can be seen within the conduit channel. The connector is inserted into the connector channel which is located on the opposing side of the conduit channel.

FIGS. 2A and 2B illustrate the embodiment of FIGS. 1A and 1B with the flexible conduit 60 shown inserted into the conduit channels 34, 36. The flexible conduit 60 is thus clipped or otherwise secured into place. The flexible conduit 60 may be removed from the conduit channels 34, 36 by first opening the valve body 14 using by unlocking the fastener 19. The flexible conduit 60 can then be pulled out of the conduit channels 34, 36 either laterally along the length of the channels 34, 36 or transversely by applying enough force to forcibly remove the flexible conduit 60 from the clipping structure of the conduit channels 34, 36. Also note that as best seen in FIG. 2A, in this embodiment the length of the connector 50 is such that it traverses the valve body 14 as well as the conduit tracks 30, 32. The length of the connector 50 may vary. In an alternative embodiment, multiple connectors 50 can be used to connect the conduit tracks to the valve body 14. For example, a first connector 50 that is secured to the conduit track 30 could partially extend into the mounting channel 15 while a second connector 50 that is secured to the other conduit track 32 could partially extend into the mounting channel 15.

Figure 3A:
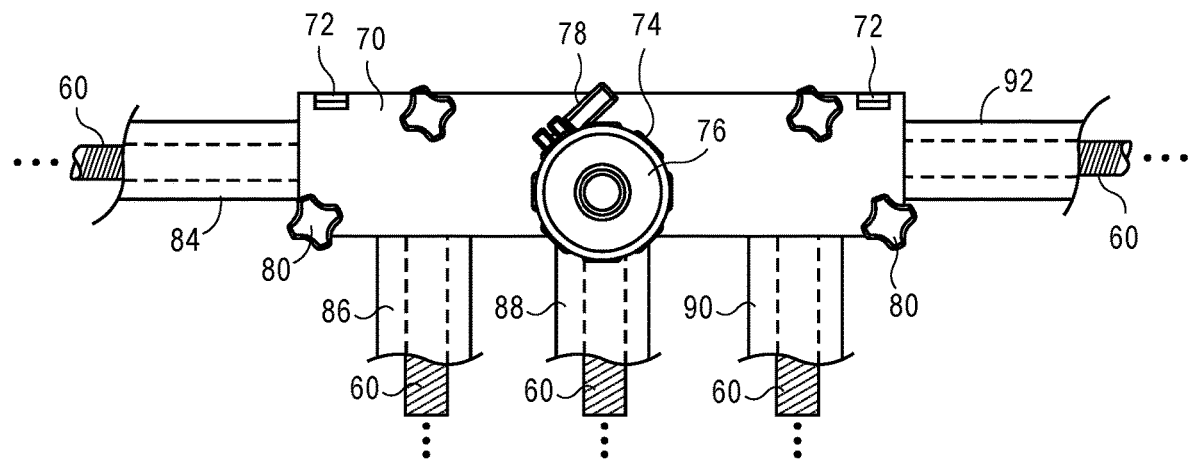
FIG. 3A illustrates another embodiment of a system for managing flexible tubing that incorporates multiple valves.
Figure 3B:
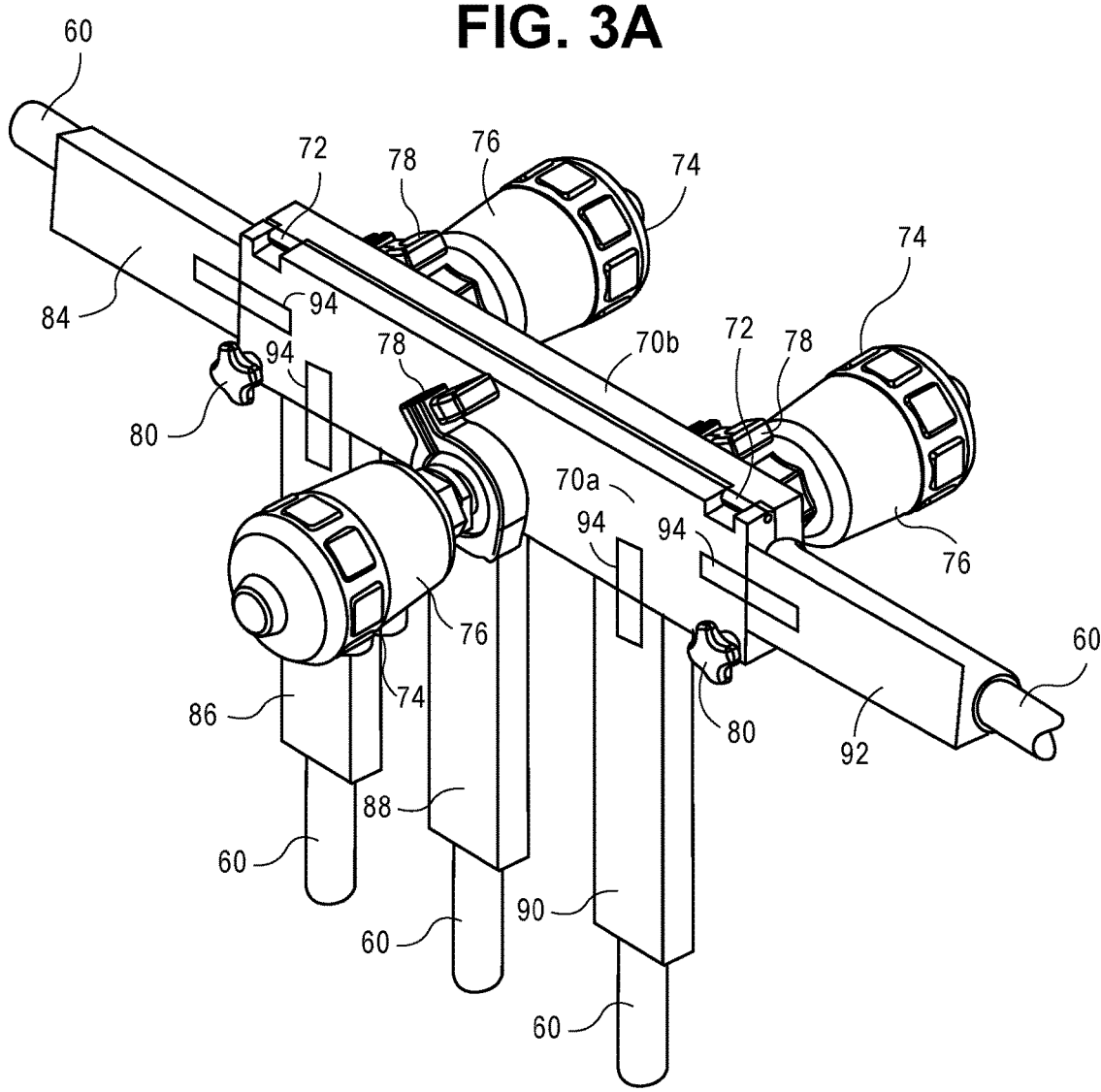
FIG. 3B is a perspective view of the system of FIG. 3A. This illustrates one valve located on one side of the valve assembly while two valves are located on an opposing side.

FIGS. 3A and 3B illustrate another embodiment of a system 10 that uses a valve assembly 70 that holds multiple valves 74 secured to the valve assembly 70 using clamps 78. The valve assembly 70 is similar to the prior embodiment in that it includes a valve body having a first half 70*a* and a second half 70*b* that are connected via a hinge 72 or multiple hinges 72. The internal surfaces of the valve assembly 70 define a passageway that holds the flexible conduit 60. In this embodiment, the flexible conduit 60 includes several branches along with a main line. The passages within the first and second halves 70*a*, 70*b* thus correspond to this branched configuration and encapsulate the flexible conduit 60. The valve assembly 70 is secured in the closed state using multiple fasteners 80 like the fasteners 19 described in the prior embodiment.

In this embodiment, there are three valves 74 that are secured to the valve assembly 70. Each valve 74 has its own actuator 76 and operates a pinching element (not shown) that works as described with respect to the embodiment of FIGS.

1A, 1B to pinch the flexible conduit 60. In this embodiment, the valves 76 are located so that fluid can be selectively switched into the various branch channels depending on which valves are opened or closed. As seen in FIGS. 3A and 3B, there are five (5) conduit tracks 84, 86, 88, 90, 92 that are connected to the valve assembly 70 and contain the flexible conduit 60 within respective conduit channels (as described previously). In this embodiment, there are separate connectors 94 that connect the various conduit tracks 84, 86, 88, 90, 92 to the valve assembly 70. Alternatively, there could be fewer connectors if one or more connectors are lengthened and inserted into multiple conduit tracks 84, 86, 88, 90, 92. The connectors 94 may formed as described above in the prior embodiments and may interface with the valve assembly 70 and the conduit tracks 84, 86, 88, 90, 92 as explained previously. Alternatively, the valve assembly 70 may have connectors 94 that are permanently formed in the valve assembly 70 and interface with the conduit tracks 84, 86, 88, 90, 92. For example, the connector 94 may include a "male" extension or connector that interfaces with corresponding "female" channels or slots formed in the conduit tracks 84, 86, 88, 90, 92 (e.g., connector channel 38, 40 of FIGS. 1A and 1B). In still another alternative construction, the conduit tracks 84, 86, 88, 90, 92 may have a male extension or connector 94 that is fixed to the respective track and interfaces with a female slot or channel (e.g., mounting channel 15 of FIGS. 1A and 1B) formed in the valve assembly 70. These alternative designs of the connectors 94 may also be used with the embodiments described in FIGS. 1A, 1B, 2A, and 2B. While three (3) valves 76 are illustrated, there could be additional or fewer valves 76 and the invention is not limited by the number of valves 76.

Figure 4B:
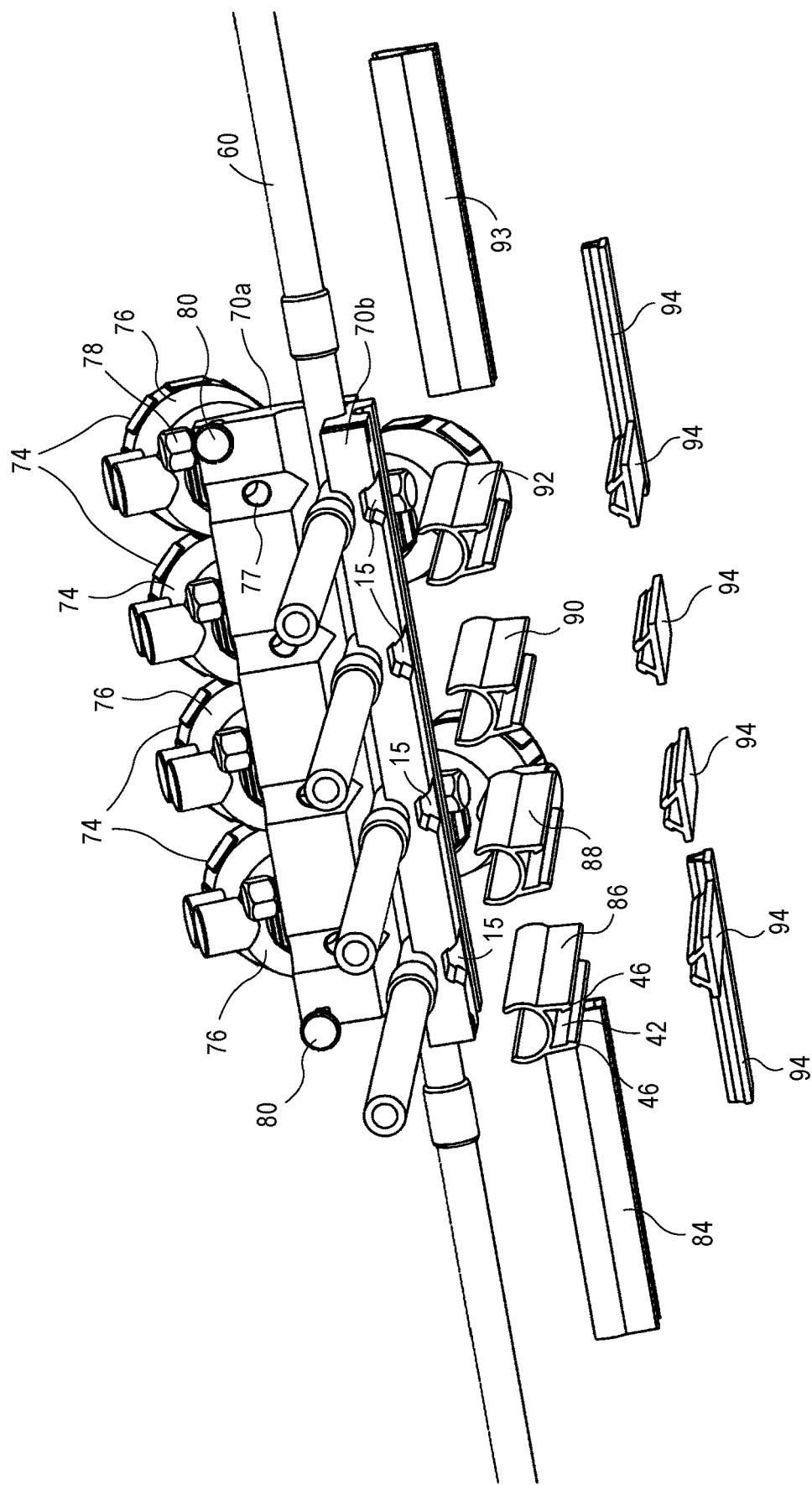
FIG. 4B illustrates another perspective view of the multi-valve embodiment of FIG. 4A.

FIGS. 4A-4C illustrate another embodiment of a system 10 that has a valve assembly 70 that includes multiple valves 74 positioned thereon. In this embodiment, there are six (6) valves 74 that are disposed on or otherwise connected to the valve assembly 70. Each valve 74 has its own actuator 76 and operates a pinching element (not shown) that works as described with respect to the embodiment of FIGS. 1A, 1B to pinch the flexible conduit 60 that is positioned between two halves 70a, 70b of the valve assembly 70 that are connected via hinge 72. Fasteners 80 (e.g., latches with knobs as described previously) may be used to secure the two halves 70a, 70b of the valve assembly 70 together. In addition, optional clamps 78 may be used to secure the valves 74 to the valve assembly 70 as illustrated. Alternatively, the valves 76 may be directly incorporated into the valve assembly 70. In this embodiment, the valves 76 are located so that fluid can be selectively switched into the various branch channels depending on which valves are opened or closed. As best seen in FIG. 4A, there are apertures 77 located in valve assembly half 70a that allow passage of the pinching element (e.g., pinching element 24 of FIG. 1C) so that the flexible conduit 60 can be pinched (closed) or un-pinched (open). Two such apertures 77 are located in the main passageway 18a while four apertures 77 are located in branch passageways 18b.

As seen in FIGS. 4A-4C, there are six (6) conduit tracks 84, 86, 88, 90, 92, 93 that are connected to the valve assembly 70 and contain the flexible conduit 60 within respective conduit channels (as described previously, for example, in FIGS. 1A, 1B, 2A, 2B). In this embodiment, there are six (6) separate connectors 94 (as described previously, for example, in FIGS. 1A, 1B, 2A, 2B) that connect the various conduit tracks 84, 86, 88, 90, 92, 93 to the valve assembly 70. As best seen in FIGS. 4B and 4C, mounting channels 15 are located in the valve assembly half 70b. The mounting channels 15 are formed as a notched channel that has notched surfaces that engage with corresponding surfaces and tabs of the connectors 94 (described previously). The connectors 94 connect the respective conduit tracks 84, 86, 88, 90, 92, 93 to the valve assembly 70 via the mounting channels 15. Note that in one alternative embodiment, a single long connector 94 could be used that connects both conduit tracks 84 and 93.

In another alternative embodiment, the connectors 94 could be omitted from the interface between the valve assembly 70 and the conduit tracks 84, 86, 88, 90, 92, 93. For example, the valve assembly 70 could have "connectors" integrated in the valve assembly 70. These, for example, could include "male" extensions that are formed integrally into the valve assembly 70 and insert into the connector channels of the conduit tracks 84, 86, 88, 90, 92, 93. In yet another alternative, the conduit tracks 84, 86, 88, 90, 92, 93 that interface with the valve assembly 70 could have "male" ends that integrate with the mounting channels 15. These alternative embodiments would eliminate the need to have connectors 94 at the interface between the conduit tracks 84, 86, 88, 90, 92, 93 and the valve assembly 70. Note that these alternative designs may also apply to the embodiments of FIGS. 1A, 1B, 2A, and 2B.

Figure 5A:
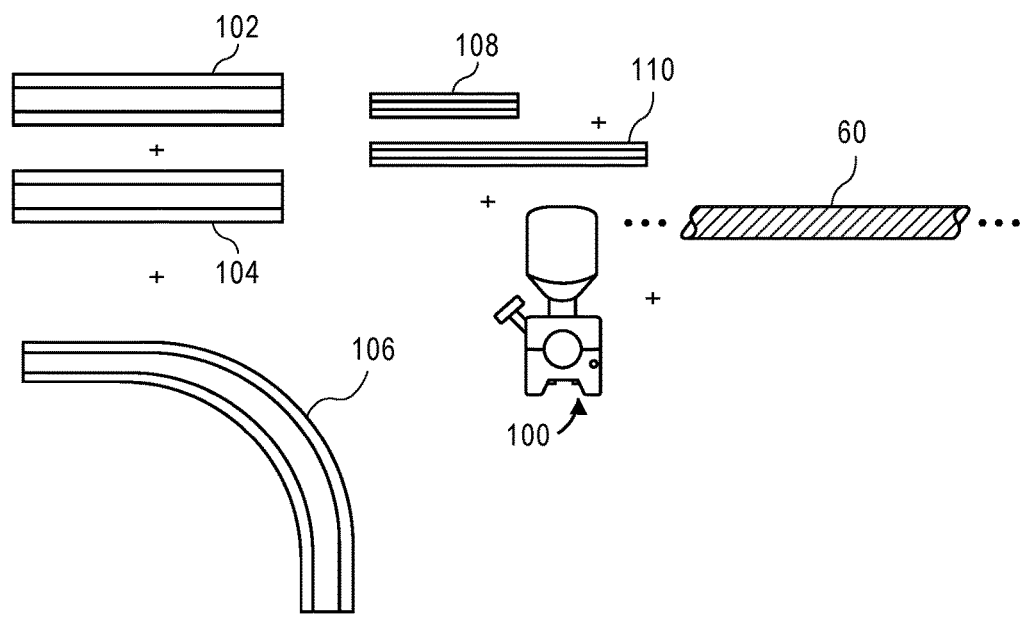
FIG. 5A illustrates an embodiment in which multiple different shapes (or lengths) of conduit tracks can be combined with other process components (e.g., a valve is illustrated) to manage the location and direction of the flexible conduit.
Figure 5B:
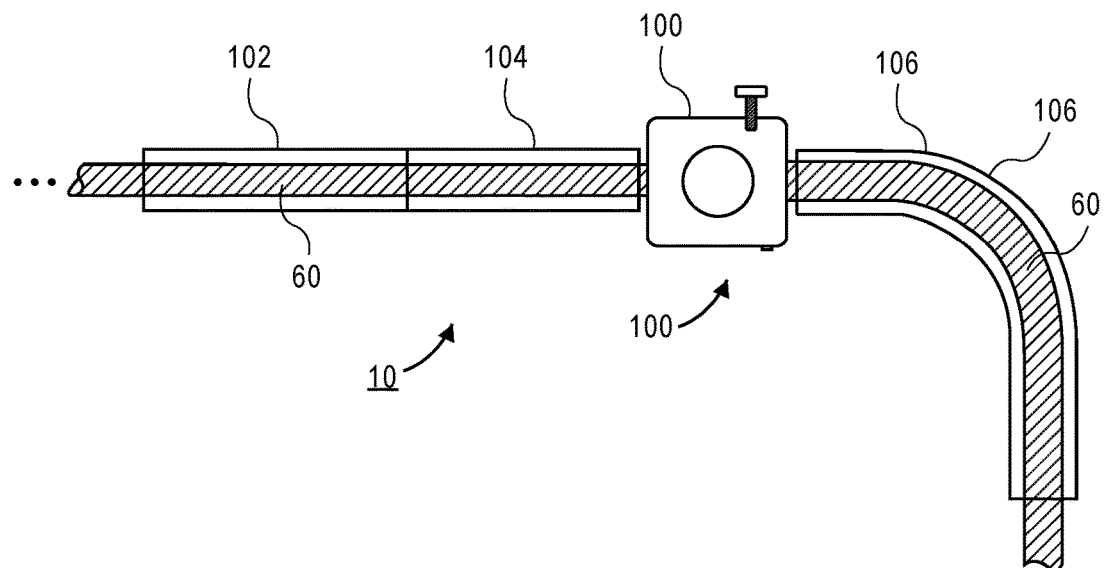
FIG. 5B illustrates the assembled components of FIG. 5A.

FIGS. 5A and 5B illustrate the modular nature of the system 10 that is described herein. Various components can be mixed and matched in various combinations and setups to achieve the desired of spatial arrangement of components. In the very basic example of FIGS. 5A and 5B a single valve 100 is illustrated along with two straight conduit tracks 102, 104 and a curved segment of conduit track 106. Two connectors 108, 110 are also illustrated. To achieve the final configuration of FIG. 5B, the two straight conduit tracks 102, 104 are connected to one another using the connector 108. The other connector 110 connects to one end of the straight conduit track (e.g., conduit track 104) and extends through the valve 100 (e.g. using a mount channel 15 of the type illustrated in FIG. 1A) and connects with the curved segment of conduit track 106. Of course, this example just illustrates a very small portion of the overall hierarchy of the system. Once can imaging that a full manufacturing process will have many different components that are connected together. Thus, many conduit tracks of a variety of different sizes, shapes, and geometries can be employed. Further, while the embodiments described herein have utilized a valve or multiple valves positioned between different conduit tracks there could be other components that are connected to conduit tracks. This includes, for example, pumps, sensors, filters, chromatography columns, reaction volumes (e.g., reactor), reservoirs, manifolds, and the like.

Figure 6:
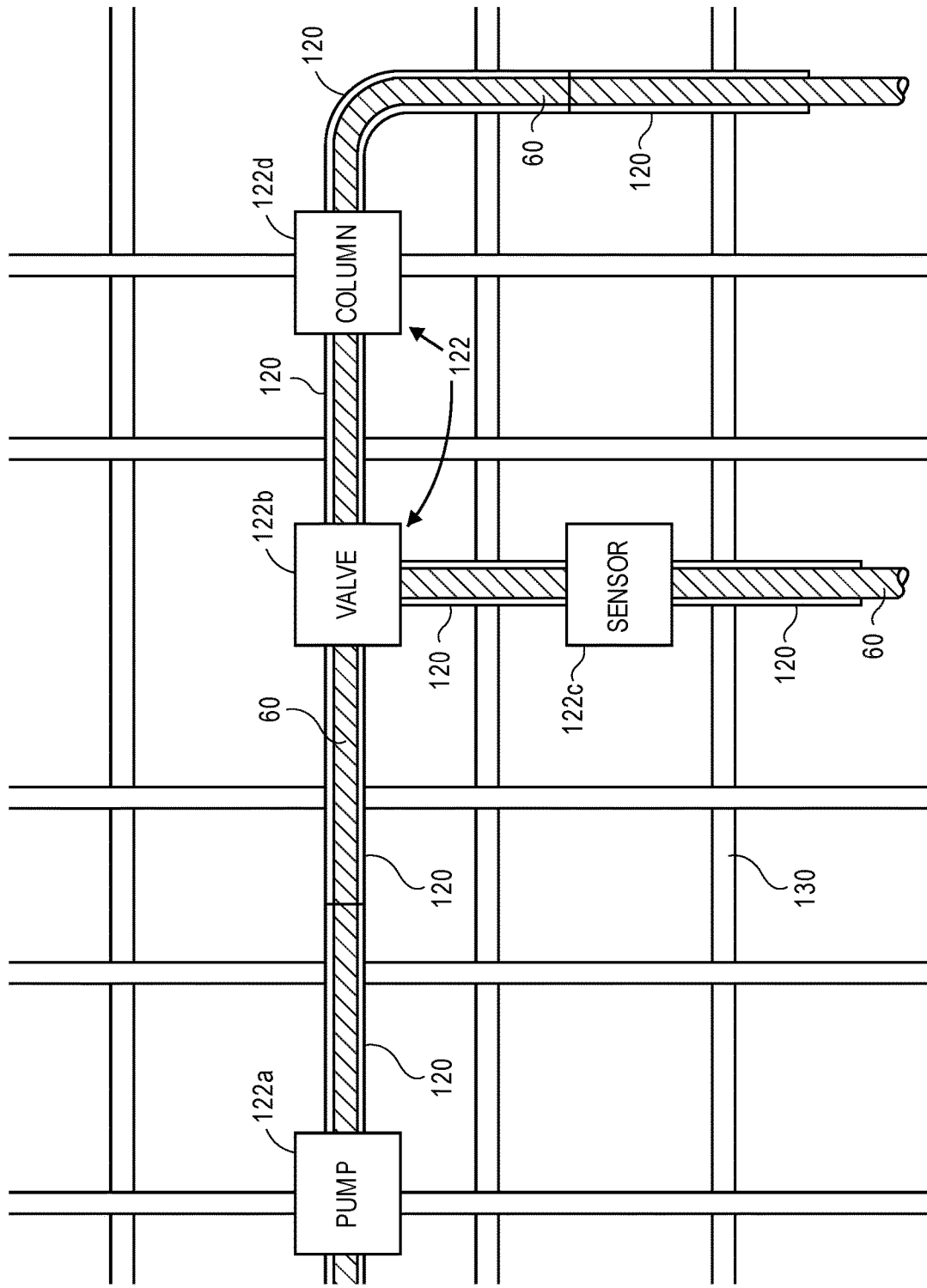
FIG. 6 illustrates an embodiment where multiple conduit tracks are connected to one another as well as different process components and hold a flexible conduit or tubing. A scaffold or support structure is illustrated which can be used to mount the conduit tracks and/or process components.

The conduit tracks with the flexible conduit 60 contained therein may be optionally mounted on a support or scaffold to further aid in spatially arranging components. The support of scaffold may be secured to the ground, ceiling (e.g., hung), or on the walls of a manufacturing facility. The scaffolding or support could also be located on a moveable cart or the like for other applications. The conduit tracks could be mounted using a variety of different fasteners such as zip ties, clips, screws, or even adhesives. FIG. 6 illustrates an embodiment where multiple conduit tracks 120 are connected to one another as well as different process components 122. Illustrated process components 122 include a pump 122a, valve 122b, sensor 122c, and column 122d, although other process components may be included. A flexible conduit or tubing 60 is illustrated being mounted in the conduit tracks 120 and passing through the various process components 122. In this embodiment, a scaffold or support 130 is also illustrated that can be used to mount the conduit tracks 120 and/or the process components 122.

As seen in the embodiments described herein, the various conduit tracks are seen as being located adjacent to the valve body or valve assembly. Note that these adjacent conduit tracks need not necessarily abut with the valve body or valve assembly. There may be a gap between an adjacent conduit track and the valve body/valve assembly. Of course, in other embodiments, the conduit tracks may physically abut with the valve body/valve assembly. Moreover, while the valve body/valve assembly has been described as interfacing with a connector, in some alternative embodiments, the valve body/valve assembly may be secured directly to the conduit track without the need for a separate connector. In addition, in the illustrated embodiments, a clamp 22, 78 is shown connecting the various valves 12, 74 and actuators 20, 76 to the valve body 14 or valve assembly 70. In some alternative embodiments, there are not clamps and the valves 12, 74 with associated actuators 20, 76 are directly secured to the valve body 14 or valve assembly 70.

Applicant has thus described a flexible conduit management system that can be used to organize and layout flexible conduit that is used as part of a liquid-based manufacturing process. The conduit tracks are used to secure the flexible conduit in a fixed location and desired shape. Each conduit track includes a conduit channel for holding the flexible conduit. The flexible conduit can easily be loaded into and out of the conduit channel. For example, for aseptic or sterile applications, the flexible conduit can quickly be replaced with another flexible conduit while using the same conduit tracks. The conduit tracks include on an opposing side a connector channel that has walls or the like to define a slot that receives a rigid or semi-rigid connector. The connector enables the conduit tracks to be connected to other conduit tracks or other process components such as valves, pumps, filters, columns, reservoirs, sensors, and the like. For example, the process component may have a mounting channel or other slot that receives the connector so that a conduit channel can be secured relative to the process component. The connector acts as a tongue that is inserted into a slot or channel on a conduit track or other process component. Various lengths of flexible conduits can be used. For example, multiple segments of flexible conduit may be connected to one another using standard connectors such as clamps can be used. Alternatively, a long length of flexible conduit that traverses many conduit tracks and process components can be used.

In the embodiments described herein the connectors may be separate in which case they are inserted into the various connector channels on the conduit tracks or mounting channels on process components. Alternatively, the connector may be fixed to a conduit track or process component and inserted into the connector channel or mounting channel of an adjacent component. It should be understood that while various embodiments are described herein various feature of one embodiment may be combined or used with another embodiment. That is to say, features of one embodiment may be substituted or used in another embodiment. While embodiments of the present invention have been shown and described, various modifications may be made without departing from the scope of the present invention. The invention, therefore, should not be limited, except to the following claims, and their equivalents.

What is claimed is:

1. A method of managing flexible conduit or tubing used in pharmaceutical, bioprocess, or food/dairy applications, the method comprising:

connecting at least two conduit tracks in an end-to-end manner with at least one connector, each conduit track including an open conduit channel disposed on a first side thereof and extending along the length of each respective conduit track and dimensioned to receive a segment of flexible silicone or polymer conduit or tubing therein, each conduit track further including a connector channel disposed on a second side thereof and extending along the length of each respective conduit track, at least a portion of the at least one connector being inserted in the connector channels of adjacent conduit tracks to connect the adjacent conduit tracks;

connecting the at least one connector to a valve body or valve assembly, via a portion of the at least one connector positioned between adjacent connected conduit tracks, to couple the adjacent connected conduit tracks to the valve body or valve assembly; and inserting one or more segments of flexible silicone or polymer conduit or tubing into the open conduit channels of the adjacent connected conduit tracks.

2. The method of claim 1, wherein one or more of the at least two conduit tracks are connected to a processing component selected from the group consisting of a pump, valve, sensor, filter, chromatography column, elution column, reactor, reservoir, and manifold.

3. The method of claim 1, further comprising removing the segment of flexible silicone or polymer conduit or tubing, and inserting another segment of flexible silicone or polymer conduit or tubing into the open conduit channels of adjacent connected conduit tracks.

4. The method of claim 1, wherein the at least two conduit tracks are mounted on a scaffold or support structure.

5. The method of claim 4, wherein the scaffold or support is stationary.

6. The method of claim 4, wherein the scaffold or support is mobile.

7. The method of claim 1, wherein the at least two conduit tracks comprise conduit tracks of different shapes.

8. The method of claim 1, wherein the at least two conduit tracks comprise conduit tracks of different lengths.

9. The method of claim 1, wherein the at least one connector comprises a base and a pair of walls extending along and away from the base, the method further comprising inserting the pair of walls of the at least one connector into the connector channels of adjacent conduit tracks to connect the adjacent conduit tracks.

10. The method of claim 9, wherein the pair of walls of the at least one connector are angled and are disposed non-orthogonal to the base, the method further comprising inserting the angled pair of walls into the connector channels of adjacent conduit tracks and engaging the angled pair of walls with the conduit tracks to connect the adjacent conduit tracks.

11. The method of claim 9, wherein inserting the pair of walls of the at least one connector into the connector channels of adjacent conduit tracks further comprises pressing the pair of walls into the connector channels to flex the pair of walls to enter the connector channels and allowing the pair of walls to engage with the connector channels to be held in place therein.

12. The method of claim 1, further comprising compressing the segment of flexible silicone or polymer conduit or tubing during insertion into the conduit channel.

13. The method of claim 1, further comprising connecting the at least one connector to a valve.

14. A method of managing flexible conduit or tubing used in pharmaceutical, bioprocess, or food/dairy applications, the method comprising:
- connecting at least two conduit tracks with a connector, each conduit track including an open conduit channel disposed on a first side thereof and extending along the length of each respective conduit track and dimensioned to receive a segment of flexible silicone or polymer conduit or tubing therein, each conduit track further including a connector channel disposed on a second side thereof and extending along the length of each respective conduit track, at least a portion of the connector being inserted in the connector channels of the at least two conduit tracks;
- inserting a segment of flexible silicone or polymer conduit or tubing into the open conduit channel of at least one of the connected conduit tracks; and
- coupling a first mating structure of the connector to a second mating structure of a valve body or valve assembly.

15. The method of claim 14, wherein the second mating structure of the valve body or valve assembly comprises a mounting channel configured to mate with first mating structure of the connector for coupling the connector to the valve body or valve assembly.

16. The method of claim 15, wherein a portion of the segment of conduit or tubing extends into a passageway in the valve body or valve assembly.

17. A method of managing flexible conduit or tubing used in a pharmaceutical, bioprocess, or food/dairy applications, the method comprising:
- inserting a segment of a first flexible conduit or tubing into a conduit channel of a first conduit track;
- inserting a segment of a second flexible conduit or tubing into a conduit channel of a second conduit track;
- coupling the first conduit track and the second conduit track to a valve body or valve assembly;
- inserting a portion of a connector into at least one of the first conduit track or the second conduit track; and
- coupling a connector to the valve body or valve assembly;
- wherein the valve assembly includes a mounting channel configured to receive a portion of the connector to couple the connector and the first and second conduit tracks to the valve body or valve assembly.

18. The method of claim 17, wherein the connector is matingly coupled with a structure on the valve body or valve assembly.

* * * * *